United States Patent

Decoster et al.

[11] Patent Number: 6,028,041
[45] Date of Patent: *Feb. 22, 2000

[54] DETERGENT COSMETIC COMPOSITIONS FOR HAIR-CARE APPLICATION AND USE THEREOF FOR CLEANSING AND CONDITIONING THE HAIR

[75] Inventors: Sandrine Decoster, Epinay sur Seine; Bernard Beauquey, Paris, both of France

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/841,790

[22] Filed: May 5, 1997

[30] Foreign Application Priority Data

May 6, 1996 [FR] France .................................. 96 05644

[51] Int. Cl.[7] .............................. C11D 9/36; C11D 3/30; C11D 3/37
[52] U.S. Cl. ...................... 510/119; 510/121; 510/122; 510/405; 510/466; 510/475; 510/476
[58] Field of Search ................... 510/119, 121, 510/122, 405, 466, 475, 476

[56] References Cited

U.S. PATENT DOCUMENTS

| | | |
|---|---|---|
| 4,710,314 | 12/1987 | Madrange et al. . |
| 5,085,857 | 2/1992 | Reid et al. ................. 424/70 |
| 5,152,914 | 10/1992 | Forster et al. ............. 252/174 |
| 5,194,260 | 3/1993 | Grollier et al. ............ 424/401 |
| 5,275,755 | 1/1994 | Sebag et al. .............. 252/174.15 |
| 5,415,857 | 5/1995 | Robbins et al. . |
| 5,439,673 | 8/1995 | Murray ...................... 424/70.12 |
| 5,470,551 | 11/1995 | Dubief et al. ............. 424/70.12 |
| 5,540,853 | 7/1996 | Trinh et al. ................ 510/101 |
| 5,656,257 | 8/1997 | Fealy et al. ............... 424/70.13 |

FOREIGN PATENT DOCUMENTS

| | | |
|---|---|---|
| 2 571 614 | 4/1986 | France . |
| 4-36225 | 2/1992 | Japan . |
| 5-332332 | 7/1995 | Japan . |
| 7-187959 | 7/1995 | Japan . |
| 8-26938 | 1/1996 | Japan . |
| 9-255536 | 3/1996 | Japan . |
| 8-217644 | 8/1996 | Japan . |
| 8-310926 | 11/1996 | Japan . |
| 9-255536 | 9/1997 | Japan . |
| 2 245 281 | 1/1992 | United Kingdom . |
| 2245281 | 1/1992 | United Kingdom . |

OTHER PUBLICATIONS

J. Knowlton et al., Handbook of Cosmetic Science and Technology, *Product Evaluation*, pp. 461–479 (1993).

J. Close, J. Soc. Cosmet. Chem., *The Concept of Sensory Quality*, pp. 95–107 (Mar./Apr. 1994).

*Primary Examiner*—Yogendra Gupta
*Assistant Examiner*—Charles Boyer
*Attorney, Agent, or Firm*—Finnegan, Henderson, Farabow, Garrett & Dunner, L.L.P.

[57] ABSTRACT

Detergent and conditioning hair-care compositions comprising, in a cosmetically acceptable medium, (A) a washing base and (B) a conditioning system comprising at least one cationic polymer and a mixture of at least one aminated silicone and at least one insoluble silicone of viscosity less than or equal to 100 Pa.s (100,000 cSt).

36 Claims, No Drawings

DETERGENT COSMETIC COMPOSITIONS FOR HAIR-CARE APPLICATION AND USE THEREOF FOR CLEANSING AND CONDITIONING THE HAIR

The present invention relates to new cosmetic compositions having improved properties, intended for simultaneously cleansing and conditioning the hair. The cosmetic composition comprises, in a cosmetically acceptable vehicle, a washing base comprising surfactants having detergent power, and as conditioning agents, cationic polymers in combination with particular silicones. The invention also relates to the use of these compositions in cosmetic applications such as, for simultaneously cleansing and conditioning the hair.

It is known in the art to use detergent hair-care compositions (or shampoos) based essentially on traditional surfactants, in particular of the anionic, nonionic and/or amphoteric type, and more especially of the anionic type for cleansing and washing the hair. These compositions are applied to wet hair, and the lather generated by massage or friction with the hands makes it possible, after rinsing with water, to remove the various kinds of soil initially present on the hair. These base compositions admittedly possess good washing power, but the intrinsic cosmetic properties which are associated with them remain, however, rather poor, in particular because the aggressive nature of such a cleansing treatment can lead eventually, on the hair fibre, to more or less pronounced damage, linked especially to the progressive removal of the lipids or proteins contained in or at the surface of the fibre.

Thus, in order to improve the cosmetic properties of the above detergent compositions, and more especially detergent compositions for application to sensitized hair (i.e., hair which is damaged or weakened, in particular through the chemical action of environmental agents and/or of hair treatments such as permanent-waving, dyeing or bleaching), it is known to introduce into these compositions supplementary cosmetic agents termed conditioning agents. The main purpose of these conditioning agents is to rectify or limit the harmful or undesirable effects induced by the various treatments or types of attack to which the hair fibres are more or less repeatedly subjected to and, of course, they can also improve the cosmetic behavior of natural hair.

The conditioning agents most commonly used to date in shampoos are cationic polymers, silicones and/or silicone derivatives which, in effect, impart to washed, dry or wet hair an ease of disentangling, softness and a smoothness which are markedly enhanced in comparison to what can be obtained with corresponding cleansing compositions which do not contain them. In addition, on sensitized hair, the use of a mixture of silicone and cationic polymer is preferred.

In spite of the progress recently made in the field of shampoos based on cationic polymers and silicone, they are not completely satisfactory. Thus, there is still at the present time a strong need for new products displaying improved performance with respect to one or more of the cosmetic properties mentioned above.

The present invention is directed towards meeting this need.

Thus, following a considerable amount of research conducted on this topic, the present inventors have, completely unexpectedly and surprisingly, discovered that, by using a combination of two particular and appropriately selected types of silicones, as defined below, in detergent hair-care compositions containing traditional cationic polymers as conditioning agents, it is possible to substantially and significantly improve the cosmetic properties associated with these compositions while preserving their good intrinsic washing power.

The compositions according to the invention impart to the hair, after rinsing, a noteworthy treatment effect which manifests itself, in particular, in an ease of disentangling as well as in providing volume, of bounce, smoothness, softness and suppleness.

All these discoveries underlie the present invention.

Thus, a subject of the present invention is new detergent and conditioning hair-care compositions comprising, in a cosmetically acceptable medium, (A) a washing base and (B) a conditioning system comprising at least one cationic polymer and a mixture of at least one aminated silicone and at least one insoluble silicone of viscosity less than or equal to 100 Pa.s (100,000 cSt).

Another subject of the invention is the use in cosmetics of the above compositions for cleansing and conditioning the hair.

However, other characteristics, aspects and advantages of the invention will become more apparent on reading the description which follows, as well as the specific, but in no way limiting, examples designed to illustrate it.

As stated above, the essential components of the hair-care products according to the invention are (A) a washing base and (B) a conditioning system comprising (i) the cationic polymer or polymers, (ii) the aminated silicone or silicones and (iii) the insoluble silicone or silicones of specific viscosity.

A—WASHING BASE:

The compositions according to the invention necessarily comprise a washing base, which is generally aqueous.

The surfactant or surfactants forming the washing base may be selected from anionic, amphoteric, nonionic and cationic surfactants and mixtures thereof.

However, according to the invention, the washing base preferably comprises anionic surfactants or mixtures of anionic surfactants and amphoteric surfactants, and still more preferably contains only anionic and amphoteric surfactants.

The minimum amount of washing base is that which is just sufficient to impart a satisfactory lathering and/or detergent power to the final composition. Excessively large amounts of washing base do not really provide any additional advantages.

Thus, according to the invention, the washing base can represent from 4% to 50% by weight, preferably from 10% to 35% by weight and still more preferably from 12% to 25% by weight of the total weight of the final composition.

The surfactants suitable for carrying out the present invention are, in particular, the following:

(i) Anionic surfactant(s):

In the context of the present invention, the nature of the anionic surfactants is not of critical importance. Thus, according to the present invention, as examples of anionic surfactants which can be used, alone or in combination, mention may preferably be made (non-limiting list) of the salts (especially alkali metal salts, in particular sodium salts, ammonium salts, amine salts, salts of amino alcohols or magnesium salts) of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefin sulphonates, paraffin sulphonates; alkylsulphosuccinates, alkyl ether sulphosuccinates, alkylamidesulphosuccinates; alkylsulphosuccinamates; alkylsulphoacetates; alkyl ether phosphates; acylsarcosinates; acylisethionates and N-acyltaurates; the alkyl or acyl radicals of all these different compounds preferably contain from 12 to 20 carbon atoms, and the aryl radical preferably denotes a phenyl or benzyl group. Among anionic surfactants which can also be used, mention may also be made of fatty acid salts such as the salts of oleic, ricinoleic, palmitic and stearic acids, and coconut oil or hydrogenated coconut oil acids; and acyllactylates in which the acyl radical contains 8 to 20 carbon atoms. It is also possible to use weakly anionic surfactants, such as alkyl D-galactosiduronic acids and their salts, as well as polyoxyalkylenated ether carboxylic acids and their salts, preferably those containing from 2 to 50 ethylene oxide groups, and mixtures thereof. The anionic surfactants of the type comprising polyoxyalkylenated ether carboxylic acids or salts are, in particular, those corresponding to formula (1):

$$R_1-(OC_2H_4)_n-OCH_2COOA \quad (1)$$

wherein:

R$_1$ represents an alkyl or alkylaryl group and n is an integer or decimal number (average value) ranging from 2 to 24 and preferably from 3 to 10, the alkyl radical having from 6 to 20 carbon atoms approximately, and aryl preferably representing phenyl, A represents H, ammonium, Na, K, Li, Mg or a monoethanolamine or triethanolamine residue. It is also possible to use mixtures of compounds of formula (I), especially mixtures in which the R$_1$ groups are different.

Among anionic surfactants, according to the invention, use may preferably be made of the salts of alkyl sulphates and of alkyl ether sulphates and mixtures thereof.

(ii) Nonionic surfactant(s):

The nonionic surfactants are compounds which are well known per se. See, in particular, "Handbook of Surfactants" by M. R. Porter, published by Blackie & Son (Glasgow and London), 1991, pp. 116–178. In the context of the present invention, the nature of the nonionic surfactants does not assume critical importance. Thus, they may be selected, in particular, from (non-limiting list) polyethoxylated, polypropoxylated or polyglycerolated alcohols, alpha-diols, alkylphenols or fatty acids, having a fatty chain containing, for example, 8 to 18 carbon atoms, it being possible for the number of ethylene oxide or propylene oxide groups to range, in particular, from 2 to 50 and for the number of glycerol groups to range, in particular, from 2 to 30. Mention may also be made of copolymers of ethylene oxide and propylene oxide, condensates of ethylene oxide and propylene oxide with fatty alcohols; polyethoxylated fatty amides preferably having from 2 to 30 mol of ethylene oxide, polyglycerolated fatty amides containing on average 1 to 5 glycerol groups, and especially 1.5 to 4; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkyl polyglycosides, N-alkylglucamine derivatives, amine oxides such as ($C_{10}$–$C_{14}$)alkylamine oxides or N-acylaminopropylmorpholine oxides. Alkyl polyglycosides are nonionic surfactants which are especially useful in the context of the present invention.

(iii) Amphoteric surfactant(s):

In the context of the present invention, the nature of the amphoteric surfactants is not of critical importance. Thus, according to the invention, amphoteric surfactants can be, in particular (non-limiting list), derivatives of secondary or tertiary aliphatic amines in which the aliphatic radical is a linear or branched chain containing from 8 to 18 carbon atoms and containing at least one anionic group conferring solubility in water (for example carboxylate, sulphonate, sulphate, phosphate or phosphonate); mention may preferably be made of ($C_8$–$C_{20}$)alkylbetaines, sulphobetaines, ($C_8$–$C_{20}$)alkylamido($C_1$–$C_6$)alkylbetaines or ($C_8$–$C_{20}$)alkylamido($C_1$–$C_6$)alkylsulphobetaines.

Among amine derivatives, mention may preferably be made of the products solid under the name MIRANOL, as are described in U.S. Pat. Nos. 2,528,378 and 2,781,354, the disclosures of which are incorporated herein by reference, and classified in the CTFA Dictionary, 3rd edition, 1982, under the names amphocarboxyglycinates and amphocarboxypropionates, corresponding to formulae (2) and (3) respectively:

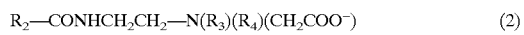

$$R_2-CONHCH_2CH_2-N(R_3)(R_4)(CH_2COO^-) \quad (2)$$

wherein

R$_2$ represents an alkyl radical of an acid R$_2$—COOH present in hydrolysed coconut oil or a heptyl, nonyl or undecyl radical, R$_3$ represents a beta-hydroxyethyl group and R$_4$ a carboxymethyl group; and

$$R_2'-CONHCH_2CH_2-N(B)(C) \quad (3)$$

wherein:

B represents —CH$_2$CH$_2$OX', C represents —(CH$_2$)$_z$—Y', with z=1 or 2,

X' represents a —CH$_2$CH$_2$—COOH group or a hydrogen atom,

Y' represents—COOH or a —CH$_2$—CHOH—SO$_3$H radical,

R$_2$' represents an alkyl radical of an acid R$_9$—COOH present in coconut oil or in hydrolysed linseed oil, an alkyl radical, in particular a C$_7$, C$_9$, C$_{11}$ or C$_{13}$ alkyl radical, a C$_{17}$ alkyl radical and its iso form or an unsaturated C$_{17}$ radical.

As an example, mention may be made of the cocoamphocarboxyglycinate sold under the trade name MIRANOL C2M concentrate by the company MIRANOL.

(iv) Cationic surfactants:

Among cationic surfactants, mention may preferably be made of (non-limiting list): the salts of primary, secondary or tertiary fatty amines, optionally polyoxyalkylenated; quaternary ammonium salts such as tetraalkylammonium, alkylamidoalkyltrialkylammonium, trialkylbenzylammonium, trialkylhydroxyalkylammonium or alkylpyridinium chlorides or bromines; imidazoline derivatives; or amine oxides having cationic character.

However, cationic surfactants do not constitute preferred surfactants for carrying out the present invention although the use of cationic surfactants is not ruled out.

B—CONDITIONING SYSTEM (i) Cationic polymer(s):

The compositions according to the invention necessarily comprise, in addition, a cationic polymer.

The conditioning agents of the cationic polymer type which can be used according to the present invention may be selected from all those which are already known per se to improve the cosmetic properties of hair treated with detergent compositions, namely, in particular, the ones described in European Patent Application No. EP-A-0 337 354 and in French Patent Application Nos. FR-A-2,270,846, 2,383,660, 2,598,611, 2,470,596 and 2,519,863, the disclosures of which are incorporated herein by reference.

In the context of the present invention, the expression "cationic polymer" means any polymer containing cationic groups and/or groups which can be ionized to cationic groups.

Preferred cationic polymers are selected from those which contain units containing primary, secondary, tertiary and/or quaternary amine groups, which can either form part of the main polymer chain or be borne by a side-chain substituent joined directly to the latter.

The cationic polymers used generally have a number-average molecular mass ranging from 500 to $5 \times 10^6$ approximately, and preferably ranging approximately from $10^3$ to $3 \times 10^6$.

Among cationic polymers, mention may preferably be made of quaternized proteins (or protein hydrolysates) and polymers of the polyamine, polyaminoamide and poly (quaternary ammonium) type. These are known products.

The quaternized proteins or protein hydrolysates are, in particular, chemically modified polypeptides bearing quaternary ammonium groups at the end of the chain or grafted onto the latter. Their molecular mass can vary, for example, from 1,500 to 10,000, and especially from 2,000 to 5,000 approximately. Among these compounds, mention may preferably be made of:

collagen hydrolysates bearing triethylammonium groups, such as the products sold under the name QUAT-PRO E by the company MAYBROOK and named in the CTFA Dictionary as triethonium hydrolyzed collagen ethosulfate;

the collagen hydrolysates bearing trimethylammonium and trimethylstearylammonium chloride groups sold under the name QUAT-PRO S by the company MAYBROOK and named in the CTFA Dictionary as steartrimonium hydrolyzed collagen;

hydrolysates of animal proteins bearing trimethylbenzylammonium groups, such as the products sold under the name CROTEIN BTA by the company CRODA and named in the CTFA Dictionary as benzyltrimonium hydrolyzed animal protein;

protein hydrolysates bearing on the polypeptide chain quaternary ammonium groups containing at least one alkyl radical having from 1 to 18 carbon atoms.

Among these protein hydrolysates, there may preferably be mentioned inter alia:

CROQUAT L, in which the quaternary ammonium groups contain a $C_{12}$ alkyl group;

CROQUAT M, in which the quaternary ammonium groups contain $C_{10}$–$C_{18}$ alkyl groups;

CROQUAT S, in which the quaternary ammonium groups contain a $C_{18}$ alkyl group;

CROTEIN Q, in which the quaternary ammonium groups contain at least one alkyl group having from 1 to 18 carbon atoms.

These different products are sold by the company Croda.

Other quaternized proteins or hydrolysates are, for example, those corresponding to formula (I):

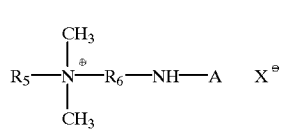

(I)

in which $X^-$ is an anion of an organic or inorganic acid, A represents a protein residue derived from collagen protein hydrolysates, $R_5$ denotes a lipophilic group containing up to 30 carbon atoms and $R_6$ represents an alkylene group having 1 to 6 carbon atoms. There may preferably be mentioned, for example, the products sold by the company Inolex under the name LEXEIN QX 3000, named in the CTFA Dictionary (4th ed. 1992) as quaternium-76 hydrolyzed collagen.

Mention may also be made of quaternized plant proteins such as wheat, maize or soya proteins. As quaternized wheat proteins, mention may preferably be made of those marketed by the company Croda under the names HYDROTRITICUM WQ or QM, named in the CTFA Dictionary as cocodimonium hydrolysed wheat protein, HYDROTRITICUM QL, nameded in the CTFA Dictionary as laurdimonium hydrolysed wheat protein, or alternatively HYDROTRITICUM QS, named in the CTFA Dictionary as steardimonium hydrolysed wheat protein.

The polymers of the polyamine, polyaminoamide and poly(quaternary ammonium) type which can be used according to the invention and which may preferably be mentioned are those described in French Patent Nos. 2,505,348 or 2,542,997, the disclosure of which are incorporated herein by reference. Among these polymers, mention may more preferably be made of:

(1) vinylpyrrolidone-dialkylaminoalkyl acrylate or methacrylate, quaternized or otherwise, such as the products sold under the name GAFQUAT by the company ISP, such as, for example, GAFQUAT 734, 755 or HS100, or alternatively the product named COPOLYMER 937. These polymers are described in detail in French Patent Nos. 2,077,143 and 2,393,573, the disclosures of which are incorporated herein by reference;

(2) cellulose ether derivatives containing quaternary ammonium groups, described in French Patent No. 1,492,597, the disclosure of which is incorporated herein by reference, and more preferably the polymers marketed under the names JR (JR 400, JR 125, JR 30M) or LR (LR 400, LR 30M) by the company Union Carbide Corporation. These polymers are also defined in the CTFA Dictionary as quaternary ammonium derivatives of hydroxyethylcellulose which has reacted with an epoxide substituted with a trimethylammonium group;

(3) cationic cellulose derivatives such as copolymers of cellulose or cellulose derivatives grafted with a water-soluble quaternary ammonium monomer, and described, in particular, in U.S. Pat. No. 4,131,576, the disclosure of which is incorporated herein by reference, such as hydroxyalkylcelluloses, for instance hydroxymethyl-, hydroxyethyl- or hydroxypropylcelluloses, grafted, preferably, with a methacryloylethyltrimethylammonium, methacrylamidopropyltrimethylammonium or dimethyidiallylammonium salt. The marketed products corresponding to this definition are, more preferably, the products sold under the name CELQUAT L 200 and CELQUAT H 100 by the company National Starch;

(4) the cationic polysaccharides described, in particular, in U.S. Pat. Nos. 3,589,578 and 4,031,307, the disclosures of which are incorporated herein by reference, such as guar gums containing trialkylammonium cationic groups. For example, guar gums modified with a 2,3-epoxypropyltrimethylammonium salt (e.g. chloride) are used. Such products are marketed, in particular, under the trade names JAGUAR C13 S, JAGUAR C 15, JAGUAR C 17 OR JAGUAR C162 by the company MEYHALL;

(5) polymers of piperazinyl units and of divalent alkylene or hydroxyalkylene radicals having unbranched or branched chains, optionally interrupted by oxygen, sulphur or nitrogen atoms or by aromatic or heterocyclic rings, as well as the oxidation and/or quaternization products of these polymers. Such polymers are described, in particular, in French Patent Nos. 2,162,025 and 2,280,361, the disclosures of which are incorporated herein by reference;

(6) water-soluble polyaminoamides prepared, in particular, by polycondensation of an acidic compound with a polyamine; these polyaminoamides may be crosslinked with an epihalohydrin, a diepoxide, a dianhydride, an unsaturated dianhydride, a bisunsaturated derivative, a bis-halohydrin, a bis-azetidinium compound, a bis-haloacyidiamine or a bis-alkyl halide, or alternatively with an oligomer resulting from the reaction of a bifunctional compound which is reactive towards a bis-halohydrin, a bis-azetidinium compound, a bis-haloacyidiamine, a bis-alkyl halide, an epihalohydrin, a diepoxide or a bisunsaturated derivative; the crosslinking agent being used in proportions ranging from 0.025 to 0.35 mol per amine group of the polyaminoamide; these polyaminoamides may be alkylated or, if they contain one or more tertiary amine functions, quaternized. Such polymers are described, in particular, in French Patent Nos. 2,252,840 and 2,368,508, the disclosures of which are incorporated by reference;

(7) polyaminoamide derivatives resulting from the condensation of polyalkylenepolyamines with polycarboxylic acids followed by an alkylation with bifunctional agents. Mention may preferably be made, for example, of adipic acid-dialkylaminohydroxyalkyldialkylenetriamine polymers in which the alkyl radical contains from 1 to 4 carbon atoms and preferably denotes methyl, ethyl or propyl. Such polymers are described, in particular, in French Patent No. 1,583,363, the disclosure of which is incorporated by reference. Among these derivatives, mention may preferably be made of the adipic acid/dimethylaminohydroxypropyldiethylenetriamine polymers sold under the name CARTARETIN F, F4 or F8 by the company Sandoz;

(8) the polymers obtained by reacting a polyalkylenepolyamine containing two primary amine groups and at least one secondary amine group with a dicarboxylic acid selected from diglycolic acid and saturated aliphatic dicarboxylic acids having from 3 to 8 carbon atoms. The mole ratio of the polyalkylenepolyamine to the dicarboxylic acid ranging from 0.8:1 to 1.4:1; the polyaminoamide resulting therefrom being reacted with epichlorohydrin in a mole ratio of epichlorohydrin relative to the secondary amine group of the polyaminoamide ranging from 0.5:1 to 1.8:1. Such polymers are described, in particular, in U.S. Pat. Nos. 3,227,615 and 2,961,347, the disclosures of which are incorporated herein by reference. Polymers of this type are marketed, in particular, under the name HERCOSETT 57 by the company Hercules Inc., or alternatively under the name PD 170 or DELSETTE 101 by the company Hercules in the case of the adipic acid/epoxypropyldiethylenetriamine copolymer;

(9) methyidiallylamine or dimethyldiallylammonium cyclohomopolymers, such as homopolymers containing as the main constituent of the chain units corresponding to formulae (VI) or (VI'):

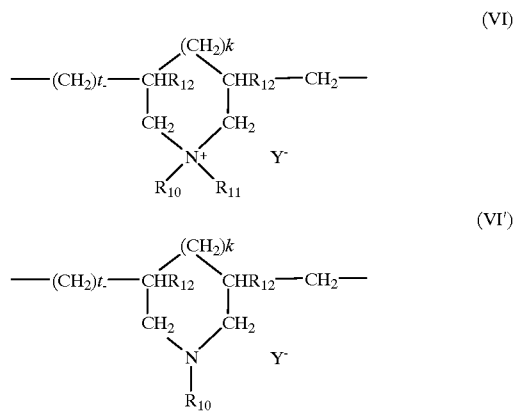

wherein k and t are equal to 0 or 1, the sum k+t being equal to 1; $R_{12}$ represents a hydrogen atom or a methyl radical; $R_{10}$ and $R_{11}$, independently of one another, represent an alkyl group having from 1 to 22 carbon atoms, a hydroxyalkyl group in which the alkyl group preferably has 1 to 5 carbon atoms or a lower amidoalkyl group, or $R_{10}$ and $R_{11}$, together with the nitrogen atom to which they are attached, can represent heterocyclic groups such as piperidyl or morpholinyl; $Y^-$ is an anion such as bromide, chloride, acetate, borate, citrate, tartrate, bisulphate, bisulphite, sulphate or phosphate. These polymers are described, in particular, in French Patent No. 2,080,759 and in its Certificate of Addition 2,190,406, the disclosures of which are incorporated herein by reference. Among the polymers defined above, mention may preferably be made of the dimethyldiallylammonium chloride homopolymer sold under the name MERQUAT 100 by the company Merck;

(10) the quaternary diammonium polymer containing repeating units corresponding to formula (VII):

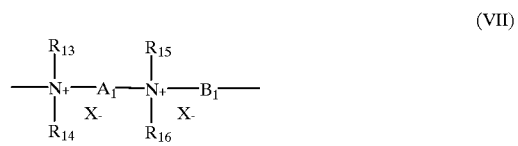

wherein:

$R_{13}$, $R_{14}$, $R_{15}$ and $R_{16}$, which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$, and $R_{16}$, together or separately, constitute, with the nitrogen atoms to which they are attached, heterocycles optionally containing a second hetero atom other than nitrogen, or alternatively $R_{13}$, $R_{14}$, $R_{15}$, and $R_{16}$ represent a linear or branched $C_1$–$C_6$ alkyl radical substituted with a nitrite, ester, acyl or amide group or —CO—O—$R_{17}$—D or —CO—NH—$R_{17}$—D where $R_{17}$ is an alkylene and D a quaternary ammonium group;

$A_1$ and $B_1$ represent polymethylene groups containing from 2 to 20 carbon atoms, which can be linear or branched and saturated or unsaturated and can contain, linked to or interposed in the main chain, one or more aromatic rings or one or more oxygen or sulphur atoms or sulphoxide, sulphone, disulphide, amino, alkylamino, hydroxyl, quaternary ammonium, ureido, amide or ester groups, and $X^-$ represents an anion derived from an inorganic or organic acid;

$A_1$, $R_{13}$ and $R_{15}$, with the two nitrogen atoms to which they are attached, can form a piperazine ring; in addition, if $A_1$ represents a linear or branched, saturated or unsaturated alkylene or hydroxyalkylene radical, $B_1$ can also represent a group $(CH_2)_n$—CO—D—OC—$(CH_2)_n$—
wherein D represents:

a) a glycol residue of formula: —O—Z—O—, where Z represents a linear or branched hydrocarbon radical or a group corresponding to one of the following formulae:

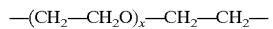

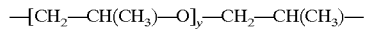

where x and y represent an integer ranging from 1 to 4 representing a defined and unique degree of polymerization, or any number ranging from 1 to 4 representing an average degree of polymerization;

b) a bis-secondary diamine residue such as a piperazine derivative;

c) a bis-primary diamine residue of formula: —NH—Y—NH—, where Y represents a linear or branched hydrocarbon radical or alternatively the bivalent radical

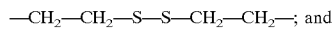; and d) a ureylene group of formula: —NH—CO—NH—.

Preferably, $X^-$ is an anion such as chloride or bromide.

These polymers have a number-average molecular mass generally ranging from 1,000 to 100,000.

Polymers of this type are described, in particular, in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosures of which are incorporated herein by reference;

(11) poly(quaternary ammonium) polymers comprising of units of formula (VIII):

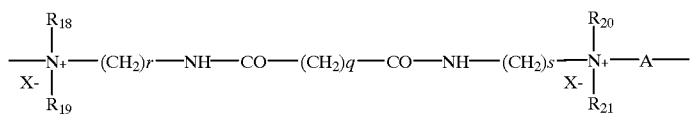

(VIII)

wherein:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2(OCH_2CH_2)_p$OH radical, where p is equal to 0 or to an integer ranging from 1 to 6, with the proviso that $R_{18}$, $R_{19}$, $R_{20}$ and $R_{21}$, do not simultaneously represent a hydrogen atom, r and s, which may be identical or different, are integers ranging from 1 to 6, q is equal to 0 or to an integer ranging from 1 to 34, X represents a halogen atom, A represents a radical of a dihalide or preferably represents —$CH_2$—$CH_2$—O—$CH_2$—$CH_2$—.

Such compounds are described, in particular, in Patent Application EP-A-122 324, the disclosure of which is incorporated herein by reference.

Among these, mention may be preferably be made of the products MIRAPOL A 15, MIRAPOL AD1, MIRAPOL AZ1 and MIRAPOL 175 sold by the company Miranol;

(12) homopolymers or copolymers derived from acrylic or methacrylic acids and containing units:

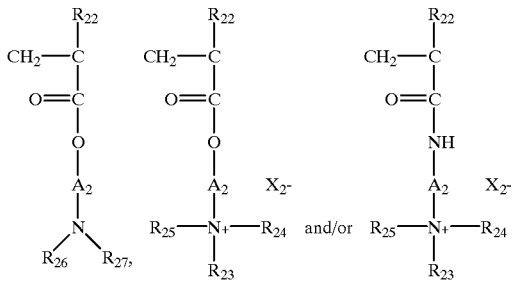

in which the groups $R_{22}$ independently represent H or $CH_3$, the groups $A_2$ independently represent a linear or branched alkyl group having 1 to 6 carbon atoms or a hydroxyalkyl group having 1 to 4 carbon atoms, the groups $R_{23}$, $R_{24}$ and $R_{25}$, which may be identical or different, independently represent an alkyl group having 1 to 18 carbon atoms or a benzyl radical, the groups $R_{26}$ and $R_{27}$, which may be identical or different, represent a hydrogen atom or an alkyl group having 1 to 6 carbon atoms, $X_2^-$ represents an anion, for example methosulphate or halide such as chloride or bromide;

The comonomer or comonomers which can be used in the preparation of the corresponding copolymers belong to the family of acrylamides, methacrylamides, diacetone acrylamides, acrylamides and methacrylamides substituted on the nitrogen with lower alkyls, alkyl esters, acrylic or methacrylic acids, vinylpyrrolidone or vinyl esters;

(13) quaternary polymers of vinylpyrrolidone and of vinylimidazole, such as, for example, the products marketed under the names LUVIQUAT FC 905, FC 550 and FC 370 by the company BASF;

(14) polyamines such as POLYQUART H sold by HENKEL, referenced under the name polyethylene glycol (15) tallow polyamine in the CTFA Dictionary; and

(15) crosslinked polymers of methacryloyloxyethyltrimethylammonium chloride, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, especially methylene(bisacrylamide). Mention may preferably be made of an acrylamide/methacryloyloxyethyltrimethylammonium chloride (20:80 by weight) crosslinked polymer, in the form of a dispersion containing 50% by weight of the said copolymer in mineral oil. This dispersion is marketed under the name SALCARE SC 92 by the company ALLIED COLLOIDS. It is also possible to use a crosslinked homopolymer of methacryloyloxyethyltrimethylammonium chloride containing approximately 50% by weight of the homopolymer in mineral oil. This dispersion is marketed under the name SALCARE SC 95 by the company ALLIED COLLOIDS.

Other cationic polymers which can be used in the context of the invention are polyalkylenimines, especially polyethylenimines, polymers containing vinylpyridine or vinylpyridinium units, condensates of polyamines and epichlorohydrin, quaternary polyureylenes and chitin derivatives.

According to the invention, mention may preferably be made of the MIRAPOL polymers referred to above, the compound of formula (VII) in which $R_{13}$, $R_{14}$, $R_{15}$ and $R_{16}$ represent a methyl radical, $A_1$ represents the radical of formula —$(CH_2)_3$— and $B_1$ represents the radical of formula —$(CH_2)_6$— and $X^-$ represents the chloride anion (referred to as MEXOMERE PO) and the compound of formula (VII) in which $R_{13}$ and $R_{14}$ represent an ethyl radical, $R_{15}$ and $R_{16}$, represent a methyl radical, $A_1$ and $B_1$ represent the radical of formula —$(CH_2)_3$— and $X^-$ represents the bromide anion (referred to as MEXOMERE PAK).

Among all the cationic polymers capable of being used in the context of the present invention, it is preferable to employ quaternary cellulose ether derivatives such as the products sold under the name JR 400 by the company UNION CARBIDE CORPORATION, cyclopolymers, more preferably the copolymers of dimethyldiallylammonium chloride and acrylamide sold under the names MERQUAT 550 and MERQUAT S by the company MERCK, and cationic polysaccharides, and still more preferably the guar gum modified with 2,3-epoxypropyltrimethylammonium chloride sold under the name JAGUAR C13S by the company MEYHALL.

According to the invention, the cationic polymer or polymers can represent from 0.001% to 10% by weight, preferably from 0.005% to 5% by weight and still more preferably from 0.01% to 3% by weight of the total weight of the final composition.

(ii) Mixture of silicones:

According to an essential characteristic of the detergent hair-care compositions according to the invention, these compositions contain, in addition, a mixture of at least one aminated silicone and at least one insoluble specific silicone (different from the aforementioned silicone) of viscosity less than or equal to 100 Pa.s (100,000 cSt). According to a preferred characteristic of the compositions according to the invention, the conditioning system associated with these compositions does not contain silicones other than the aminated silicones and the insoluble silicones of viscosity according to the invention.

(1)—Aminated silicone(s)

According to the invention, the term "aminated silicone" denotes any silicone containing at least one primary, secondary or tertiary amine or a quaternary ammonium group. The following may thus be mentioned:

(a) the polysiloxanes named in the CTFA Dictionary as amodimethicone and corresponding to formula (II):

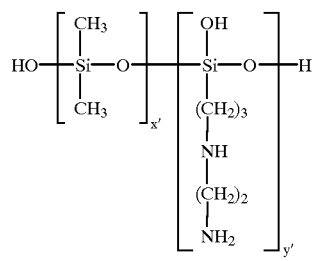

in which x' and y' are integers depending on the molecular weight, generally such that the said number-average molecular weight ranges from 5,000 to 500,000 approximately;

(b) the cationic silicone polymers corresponding to formula (III):

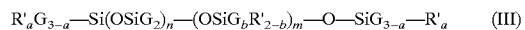

wherein:

G is a hydrogen atom or a phenyl, OH or $C_1$–$C_8$ alkyl group, for example methyl, a represents the number 0 or an integer from 1 to 3, preferably 0, b represents 0 or 1, and preferably 1, m and n are numbers such that the sum (n+m) can vary, preferably, from 1 to 2,000, and more preferably from 50 to 150, it being possible for n to represent a number from 0 to 1,999 and preferably from 49 to 149 and for m to represent a number from 1 to 2,000 and preferably from 1 to 10;

R' is a monovalent radical of formula —$C_qH_{2q}L$ in which q is a number from 2 to 8 and L is an optionally quaternized amino group selected from the groups:
—NR"—$CH_2$—$CH_2$—N'(R")$_2$;
—N(R")$_2$;
—N$^\oplus$(R")$_3$A$^-$;
—N$^\oplus$(R")$_2$HA$^-$;
—N$^\oplus$H$_2$(R")A$^-$; and
—N(R")—$CH_2$—$CH_2$—N$^\oplus$R"H$_2$A$^-$ wherein R" represents hydrogen, phenyl, benzyl or a saturated monovalent hydrocarbon radical, for example an alkyl radical having from 1 to 20 carbon atoms, and A$^-$ represents a halide ion such as, for example, fluoride, chloride, bromide or iodide.

A product corresponding to this definition is the polymer named trimethylsilylamodimethicone, which corresponds to formula (IV):

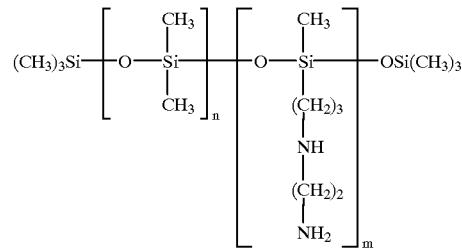

wherein n and m have the meanings given above (see formula III).

Such polymers are described, for example, in European Patent Application No. EP-A-95238, the disclosure of which is incorporated herein by reference.

(c) the cationic silicone polymers corresponding to formula (V):

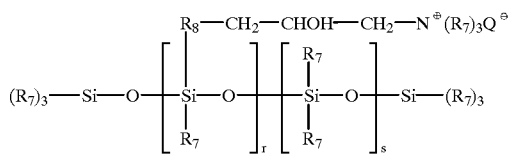

wherein:
$R_7$ represents a monovalent hydrocarbon radical having from 1 to 18 carbon atoms, and preferably a $C_1$–$C_{18}$ alkyl or $C_2$–$C_{18}$ alkenyl radical, for example methyl;

$R_8$ represents a divalent hydrocarbon radical, in particular a $C_1$–$C_{18}$ alkylene radical or a divalent $C_1$–$C_{18}$, for example $C_1$–$C_8$, alkylenoxy radical;

$Q^-$ is a halide ion, preferably chloride;

r represents an average statistical value ranging from 2 to 20, and preferably from 2 to 8;

s represents an average statistical value from 20 to 200, and preferably from 20 to 50.

Such polymers are described in U.S. Pat. No. 4,185,087, the disclosure of which is incorporated herein by reference.

A polymer falling within this class is the polymer sold by the company Union Carbide under the name UCAR SILICONE ALE 563.

When these silicone polymers are employed, an especially advantageous embodiment is their joint use with cationic and/or nonionic surfactants. It is possible to use, for example, the product sold under the name CATIONIC EMULSION DC 929 by the company Dow Corning, which comprises, besides amodimethicone, a cationic surfactant comprising a mixture of products corresponding to the formula:

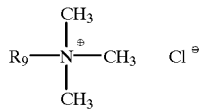

wherein
$R_9$ represents alkenyl and/or alkyl radicals having from 14 to 22 carbon atoms, derived from tallow fatty acids, in combination with a nonionic surfactant of formula:

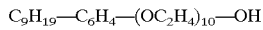

known under the name NONOXYNOL 10.

It is also possible to use, for example, the product sold under the name CATIONIC EMULSION DC 939 by the company Dow Corning, which comprises, besides amodimethicone, a cationic surfactant, trimethylcetylammonium chloride, in combination with a nonionic surfactant, trideceth-12.

Another commercial product which can be used according to the invention is the product sold under the name DOW CORNING Q2 7224 by the company Dow Corning, containing, in combination, the trimethylsilylamodimethicone of formula (IV), a nonionic surfactant of formula: $C_8H_{17}$—$C_6H_4$—$(OCH_2CH_2)_n$—OH where n=40, also named octoxynol-40, another nonionic surfactant of formula: $C_{12}H_{25}$—$(OCH_2CH_2)_n$—OH where n=6, also named isolaureth-6, and glycol.

The hair-care compositions according to the invention contain the aminated silicones defined above in weight contents which can range from 0.05% to 10%, preferably from 0.1% to 5% and still more preferably from 0.2% to 3% relative to the total weight of the composition.

(2)—Insoluble silicone(s) of viscosity less than or equal to 100,000 cSt (100 Pa.s):

The viscosity of these insoluble silicones preferably ranges from 1,000 to 100,000 and more preferably from 20,000 to 80,000 cSt (from 20 to 80 Pa.s).

The viscosity of these silicones is measured at 25° C. according to ASTM Standard 445 Appendix C.

In the context of the present invention, the term "insoluble" is understood to mean insoluble in the final composition.

In the context of the present invention, the term "silicone" is understood to mean, in conformity with the generally accepted definition, all organosilicon polymers or oligomers having a linear or cyclic, branched or crosslinked structure, of variable molecular weight, obtained by polymerization and/or polycondensation of appropriately functionalized silanes, and comprising in essence a repetition of main units in which the silicon atoms are joined to one another by oxygen atoms (siloxane link ≡Si—O—Si≡), optionally substituted hydrocarbon radicals being linked directly via a carbon atom to the said silicon atoms. The most common hydrocarbon radicals are alkyl radicals, in particular $C_1$–$C_{10}$ alkyl radicals and especially methyl, fluoroalkyl radicals, and aryl radicals and especially phenyl.

According to the invention, the silicone of appropriate viscosity is preferably selected from:

(i) polydialkylsiloxanes;
(ii) polydiarylsiloxanes; and
(iii) polyalkylarylsiloxanes.

Among polydialkylsiloxanes, mention may preferably be made of:

linear polydimethylsiloxanes containing terminal trimethylsilyl groups, such as, for example, and without implied limitation, the SILBIONE oils of the 70047 series, marketed by RHONE-POULENC, linear polydimethylsiloxanes containing terminal hydroxydimethylsilyl groups, such as the oils of the 48 V series from RHONE-POULENC.

In this class of polydialkylsiloxanes, mention may more preferably be made of the polyalkylsiloxanes sold by the company GOLDSCHMIDT under the trade names ABILWAX 9800 and ABILWAX 9801, which are poly($C_1$–$C_{20}$) alkylsiloxanes.

Among polyalkylarylsiloxanes, mention may preferably be made of linear or branched polydimethylmethylphenylsiloxanes or polydimethyldiphenylsiloxanes, such as the product DC 556 COSMETIC GRAD FLUID from DOW CORNING.

According to the invention, the silicone of viscosity less than 100,000 cSt preferably does not contain an amine or ammonium function.

The hair-care compositions according to the invention contain the silicones of appropriate viscosity, defined above, in weight contents which can range from 0.05% to 10%, preferably from 0.1% to 5% and still more preferably between 0.2% to 3% relative to the total weight of the composition.

The vehicle or carrier of the detergent compositions according to the invention is preferably water or an aqueousalcoholic solution of a lower alcohol such as ethanol, isopropanol or butanol.

The detergent compositions according to the invention have a final pH generally ranging from 3 to 10. Preferably, the pH ranges from 5 to 8. Adjustment of the pH to the desired value may be done in the traditional manner by adding a base (organic or inorganic) to the composition, for example aqueous ammonia or a primary, secondary or tertiary (poly)amine such as monoethanolamine, diethanolamine, triethanolamine, isopropanolamine or 1,3-propanediamine, or alternatively by adding an acid, preferably a carboxylic acid such as, for example, citric acid.

The detergent compositions according to the invention may naturally contain, in addition, all the standard adjuvants encountered in the field of shampoos, such as, for example, perfumes, preservatives, sequestering agents, thickeners, emollients, foam modifiers, colorants, pearlescent agents, hydrating agents, antidandruff or antiseborrhoeic agents, vitamins, sunscreen agents, suspending agents and the like.

Naturally, a person skilled in the art will take care to choose this/these possible supplementary compound(s) and/ or the amounts thereof in such a way that the advantageous properties intrinsically associated with the quaternary combination (washing base+cationic polymer+two specific silicones) according to the invention are not, or are not substantially, impaired by the addition or additions envisaged.

These compositions may take the form of more or less thickened liquids, of creams or of gel, and they are mainly suitable for washing the hair, for hair care and/or for hair styling. They may also take the form of lotions to be rinsed.

When the compositions according to the invention are employed as traditional shampoos, they are simply applied to wet hair, and the lather generated by massage or friction with the hands is then removed, after an optional period of exposure, by rinsing with water, it being possible for the operation to be repeated once or several times.

Another subject of the invention is a process for washing and conditioning keratinous fibres such as the hair, comprising the steps of applying to the fibres in the wet state an effective amount of a composition as defined above, and in then rinsing with water after an optional period of exposure.

As stated above, the compositions according to the invention impart to the hair, after rinsing, a noteworthy styling effect which manifests itself, in particular, in an ease of styling and of hold as well as in a provision of volume and of bounce which are markedly improved.

A specific but in no way limiting example illustrating the invention will now be given.

EXAMPLE

Three shampoo compositions were produced, one according to the invention (composition A) and the other two comparative (compositions B and C):

| | A Invention | B Comparative | C Comparative |
|---|---|---|---|
| Sodium lauryl ether sulphate ($C_{12}/C_{14}$ in the ratio 70:30) containing 2.2 mol of ethylene oxide (AS = active substance) | 14 g AS | 14 g AS | 14 g AS |
| MIRANOL C2M (*) | 4.6 g AS | 4.6 g AS | 4.6 g AS |
| Cationic polymer (**) | 0.1 g | 0.1 g | 0.1 g |

-continued

| | A Invention | B Comparative | C Comparative |
|---|---|---|---|
| Aminated silicone (***) | 1.05 g AS | — | 1.05 g AS |
| Silicone < 100,000 cSt (60,000 cSt) (****) | 2 g | 2 g | — |
| Silicone > 100,000 cSt (300,000 cSt) (*****) | — | — | 2 g |
| Mixture of 1-(hexa-decyloxy) octadodecanol and cetyl alcohol | 2.5 g | 2.5 g | 2.5 g |
| Coconut acid monoisopropanolamide | 0.6 g | 0.6 g | 0.6 g |
| Citric acid qs pH | 5.2 | 5.2 | 5.2 |
| Demineralized water qs | 100 g | 100 g | 100 g |

(*): Sodium cocamidoethyl-N-hydroxyethyl-N-carboxymethylglycinate sold by RHONE POULENC
(**): Guar gum modified with 2,3-epoxypropyltrimethylammonium chloride, sold under the name JAGUAR C13S by the company RHONE POULENC
(***): Amodimethicone sold in cationic emulsion containing 35% of active substance under the name FLUID DC 939 by the company DOW CORNING
(****): Polydimethylsiloxane of viscosity 60,000 cSt sold by the company DOW CORNING under the name FLUID DC 200 - 60,000 cSt
(*****): Polydimethylsiloxane of viscosity 300,000 cSt sold by the company WACKER under the name AK 300,000.

Shampooing was performed by applying approximately 12 g of the composition A to previously wefted hair. The shampoo was worked to a lather and the hair was then rinsed copiously with water.

The same procedure as above was adopted with the comparative compositions B and C.

A panel of experts evaluated the disentangling of the wet hair, the disentangling of the dried hair, the ease of shaping, the softness and the smoothness of the dried hair.

All the experts noted a marked improvement of these properties in the case of the hair treated with the composition A according to the invention.

What is claimed is:

1. A detergent and conditioning hair-care composition, comprising, in a cosmetically acceptable medium: (A) a washing base; and (B) a conditioning system comprising at least one cationic polymer, at least one aminated silicone and at least one insoluble silicone of viscosity from 20,000 to 80,000 cSt, said insoluble silicone being different from said aminated silicone.

2. A composition according to claim 1, wherein said washing base comprises one or more surfactants selected from anionic, amphoteric, nonionic and cationic surfactants and mixtures thereof.

3. A composition according to claim 1, wherein said washing base is present in an amount ranging from 4 weight % to 50 weight %, relative to the total weight of the composition.

4. A compositions according to claim 3, wherein said washing base is present in an amount ranging from 10 weight % to 35 weight %, relative to the total weight of the composition.

5. A composition according to claim 4, wherein said washing base is present in an amount ranging from 12 weight % to 25 weight %, relative to the total weight of the composition.

6. A composition according to claim 1, wherein said at least one cationic polymer is present in an amount ranging from 0.001 weight % to 10 weight %, relative to the total weight of the composition.

7. A composition according to claim 6, wherein said at least one cationic polymer is present in an amount ranging from 0.005 weight % to 5 weight %, relative to the total weight of the composition.

8. A composition according to claim 7, wherein said at least one cationic polymer is present in an amount ranging from 0.01 weight % to 3 weight %, relative to the total weight of the composition.

9. A composition according to claim 1, wherein said at least one insoluble silicone is present in an amount ranging from 0.05 weight % to 10 weight %, relative to the total weight of the composition.

10. A composition according to claim 9, wherein said at least one insoluble silicone is present in an amount ranging from 0.1 weight % to 5 weight %, relative to the total weight of the composition.

11. A composition according to claim 10, wherein said at least one insoluble silicone is present in an amount ranging from 0.2 weight % to 3 weight %, relative to the total weight of the composition.

12. A composition according to claim 1, wherein said at least one aminated silicone is present in an amount ranging from 0.05 weight % to 10 weight %, relative to the total weight of the composition.

13. A composition according to claim 12, wherein said at least one aminated silicone is present in an amount ranging from 0.1 weight % to 5 weight %, relative to the total weight of the composition.

14. A composition according to claim 1, wherein said at least one cationic polymer is a quaternary cellulose ether derivative, a cyclopolymer, a cationic polysaccharide or a mixture thereof.

15. A composition according to claim 14, wherein said cyclopolymer is a copolymer of dimethyldiallylammonium chloride and acrylamide.

16. A composition according to claim 14, wherein said quaternary cellulose ether derivative is a hydroxyethylcellulose which has been reacted with an epoxide substituted with a trimethylammonium group.

17. A composition according to claim 14, wherein said cationic polysaccharides is a guar gum modified with a 2,3-epoxypropyltrimethylammonium salt.

18. A composition according to claim 1, wherein said at least one insoluble silicone has a viscosity ranging from 20 to 60 Pa.s (from 20,000 to 60,000 cSt).

19. A composition according to claim 1, wherein said at least one insoluble silicone is selected from (i) polydialkylsiloxanes, (ii) poly-diarylsiloxanes and (iii) poly-alkylarylsiloxanes.

20. A composition according to claim 1, wherein said at least one aminated silicone is selected from:

(a) polysiloxanes corresponding to the formula:

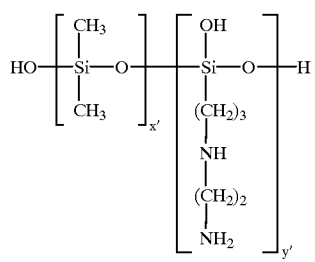

(II)

wherein x' and y' are integers such that the number average molecular weight ranges from 5,000 to 500,000;

(b) cationic silicone polymers of formula (III):

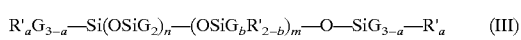

(III)

wherein:
G is a hydrogen atom, a phenyl, OH or $C_1$–$C_8$ alkyl group,
a represents the number 0 or an integer from 1 to 3,
b represents 0 or 1,
m and n are numbers such that the sum (n+m) ranges from 1 to 2,000, it being possible for n to represent a number ranging from 0 to 1,999 and for m to represent a number from 1 to 2,000;
R' is a monovalent radical of formula —$C_qH_{2q}$L wherein q is a number from 2 to 8 and L is an optionally quaternized amino group selected from:
—NR"—$CH_2$—$CH_2$—N'(R")$_2$;
—N(R")$_2$;
—N$^\oplus$(R")$_3$A$^-$;
—N$^\oplus$H(R")$_2$A$^-$;
—N$^\oplus$H$_2$(R")A$^-$; or
—N(R")—$CH_2$—$CH_2$—N$^\oplus$R"H$_2$A$^-$,
wherein R" represents hydrogen, phenyl, benzyl or a saturated monovalent hydrocarbon radical, and A$^-$ represents a halide ion;

(c) cationic silicone polymers corresponding to formula (V):

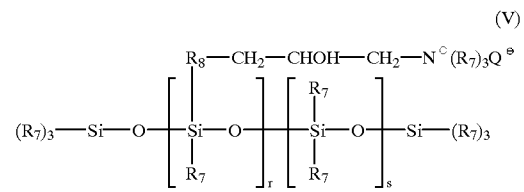

(V)

wherein:
$R_7$ represents a monovalent hydrocarbon radical having from 1 to 18 carbon atoms;
$R_8$ represents a divalent hydrocarbon radical
Q$^-$ is a halide ion;
r represents an average statistical value ranging from 2 to 20; and
s represents an average statistical value ranging from 20 to 200.

21. A composition according to claim 20, wherein G is methyl.

22. A composition according to claim 20, wherein a is 0.

23. A composition according to claim 20, wherein b is 1.

24. A composition according to claim 20, wherein n ranges from 49 to 149, m ranges from 1 to 10, and said sum (n+m) ranges from 50 to 150.

25. A composition according to claim 20, where R" is an alkyl radical having from 1 to 20 carbon atoms.

26. A composition according to claim 20, wherein Q$^-$ is a chloride ion.

27. A composition according to claim 20, wherein $R_7$ is a $C_1$–$C_{18}$ alkyl or a $C_2$–$C_{18}$ alkenyl radical.

28. A composition according to claim 20, wherein $R_8$ is a $C_1$–$C_{18}$ alkylene radical or a divalent $C_1$–$C_{18}$ alkylenoxy radical.

29. A composition according to claim 20, wherein r ranges from 2 to 8.

30. A composition according to claim 20, wherein s ranges from 20 to 50.

31. A composition according to claim 1, wherein said composition has a pH ranging from 3 to 10.

32. A composition according to claim 1, wherein said conditioning system is free from silicones other than said at least one aminated silicone and said at least one insoluble silicone.

33. A composition according to claim 1, wherein said at least one insoluble silicone does not contain an amine or ammonium function.

34. A process for washing and conditioning keratinous fibres comprising the steps of applying to said fibres in a wet state an effective amount of a composition as defined in claim 1, and then rinsing with water after an optional period of exposure.

35. A process according to claim 34, wherein said keratinous fibres are hair.

36. A detergent and conditioning hair-care composition, comprising, in a cosmetically acceptable medium: (A) a washing base; and (B) a conditioning system comprising at least one cationic polymer, at least one aminated silicone and at least one insoluble silicone of viscosity 60,000 cSt, said insoluble silicone being different from said aminated silicone.

* * * * *

UNITED STATES PATENT AND TRADEMARK OFFICE
CERTIFICATE OF CORRECTION

PATENT NO.: 6,028,041

DATED: February 22, 2000

INVENTOR(S): Sandrine Decoster and Bernard Beauquey

It is certified that an error appears in the above-identified patent and that said Letters Patent is hereby corrected as shown below:

In claim 4, column 16, line 52, change "compositions" to --composition--.

In claim 20, column 18, in Fig. (V), change "N°" to --N°--.

Signed and Sealed this

Fourteenth Day of November, 2000

*Attest:*

Q. TODD DICKINSON

*Attesting Officer*      *Director of Patents and Trademarks*